(12) United States Patent
Karnowski et al.

(10) Patent No.: US 8,218,838 B2
(45) Date of Patent: Jul. 10, 2012

(54) METHOD AND SYSTEM FOR ASSIGNING A CONFIDENCE METRIC FOR AUTOMATED DETERMINATION OF OPTIC DISC LOCATION

(75) Inventors: Thomas P. Karnowski, Knoxville, TN (US); Kenneth W. Tobin, Jr., Harriman, TN (US); Vijaya Priya Muthusamy Govindasamy, Knoxville, TN (US); Edward Chaum, Memphis, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 734 days.

(21) Appl. No.: 12/263,876

(22) Filed: Nov. 3, 2008

(65) Prior Publication Data
US 2010/0278398 A1 Nov. 4, 2010

(51) Int. Cl.
*G06K 9/60* (2006.01)
(52) U.S. Cl. .......................... 382/128; 382/117; 351/200
(58) Field of Classification Search .................. 382/128, 382/195, 201; 356/388
See application file for complete search history.

(56) References Cited

U.S. PATENT DOCUMENTS

| | | | |
|---|---|---|---|
| 5,233,517 A | 8/1993 | Jindra | |
| 5,270,924 A | 12/1993 | Hideshima | |
| 5,579,471 A | 11/1996 | Barber et al. | |
| 5,868,134 A | 2/1999 | Sugiyama et al. | |
| 5,878,746 A | 3/1999 | Lemelson et al. | |
| 5,911,139 A | 6/1999 | Jain et al. | |
| 6,053,865 A | 4/2000 | Sugiyama et al. | |
| 6,104,828 A | 8/2000 | Shioiri | |
| 6,115,489 A | 9/2000 | Gupta et al. | |
| 6,285,995 B1 | 9/2001 | Abdel-Mottaleb et al. | |
| 6,292,577 B1 | 9/2001 | Takahashi | |
| 6,415,173 B1 | 7/2002 | Sponsel et al. | |
| 6,523,954 B1 | 2/2003 | Kennedy et al. | |

(Continued)

FOREIGN PATENT DOCUMENTS
EP 990997 4/2000

OTHER PUBLICATIONS

Goldbaum et al., Automated Diagnosis and Image Understanding with Object Extraction, Object Classification, and Inferencing in Retinal Images, 1996, IEEE Proceedings, Int'l Conf on Image Processing, vol. 3, pp. 695-698.

(Continued)

*Primary Examiner* — Wensing Kuo
(74) *Attorney, Agent, or Firm* — Novak Druce + Quigg LLP (57) ABSTRACT

A method for assigning a confidence metric for automated determination of optic disc location that includes analyzing a retinal image and determining at least two sets of coordinates locating an optic disc in the retinal image. The sets of coordinates can be determined using first and second image analysis techniques that are different from one another. An accuracy parameter can be calculated and compared to a primary risk cut-off value. A high confidence level can be assigned to the retinal image if the accuracy parameter is less than the primary risk cut-off value and a low confidence level can be assigned to the retinal image if the accuracy parameter is greater than the primary risk cut-off value. The primary risk cut-off value being selected to represent an acceptable risk of misdiagnosis of a disease having retinal manifestations by the automated technique.

20 Claims, 3 Drawing Sheets

U.S. PATENT DOCUMENTS

| | | |
|---|---|---|
| 6,556,853 B1 | 4/2003 | Cabib et al. |
| 6,560,476 B1 | 5/2003 | Pelletier et al. |
| 6,678,703 B2 | 1/2004 | Rothschild et al. |
| 6,690,828 B2 | 2/2004 | Meyers |
| 6,751,363 B1 | 6/2004 | Natsev et al. |
| 6,891,920 B1 | 5/2005 | Minyard et al. |
| 6,934,698 B2 | 8/2005 | Judd et al. |
| 6,993,161 B2 | 1/2006 | Marshall et al. |
| 6,996,260 B1 | 2/2006 | Skands et al. |
| 7,027,633 B2 | 4/2006 | Foran et al. |
| 7,031,555 B2 | 4/2006 | Troyanker |
| 7,043,474 B2 | 5/2006 | Mojsilovic et al. |
| 7,110,582 B1 | 9/2006 | Hay |
| 7,187,786 B2 | 3/2007 | Kee |
| 7,220,000 B2 | 5/2007 | Alster et al. |
| 7,228,006 B2 | 6/2007 | Stubler et al. |
| 7,244,230 B2 | 7/2007 | Duggirala et al. |
| 7,310,651 B2 | 12/2007 | Dave et al. |
| 7,374,077 B2 | 5/2008 | Shimura |
| 2001/0043729 A1 | 11/2001 | Giger et al. |
| 2002/0021828 A1 | 2/2002 | Papier et al. |
| 2002/0039434 A1 | 4/2002 | Levin et al. |
| 2002/0052551 A1 | 5/2002 | Sinclair et al. |
| 2003/0026470 A1 | 2/2003 | Kasai |
| 2003/0071970 A1 | 4/2003 | Donnerhacke et al. |
| 2003/0103663 A1 | 6/2003 | Li et al. |
| 2003/0229278 A1 | 12/2003 | Sinha |
| 2004/0003001 A1 | 1/2004 | Shimura |
| 2004/0024758 A1 | 2/2004 | Iwasaki |
| 2004/0071368 A1 | 4/2004 | Chadha et al. |
| 2004/0085542 A1 | 5/2004 | Soliz et al. |
| 2004/0105074 A1 | 6/2004 | Soliz et al. |
| 2004/0151379 A1 | 8/2004 | Kim et al. |
| 2005/0021512 A1 | 1/2005 | Koenig |
| 2005/0038678 A1 | 2/2005 | Qian et al. |
| 2005/0057721 A1 | 3/2005 | Kolanko et al. |
| 2005/0094099 A1 | 5/2005 | Newman et al. |
| 2005/0171974 A1 | 8/2005 | Doering |
| 2005/0210015 A1 | 9/2005 | Zhou et al. |
| 2006/0112092 A1 | 5/2006 | Ziou et al. |
| 2006/0147095 A1* | 7/2006 | Usher et al. ............... 382/117 |
| 2006/0147099 A1 | 7/2006 | Marshall et al. |
| 2007/0109499 A1* | 5/2007 | Yan et al. ................ 351/221 |
| 2007/0127795 A1 | 6/2007 | Lau et al. |

OTHER PUBLICATIONS

Gupta et al., Content-Based Retrieval of Opthalmological Images, 1996, IEEE Proceedings, Int'l Conf on Image Processing, vol. 3, pp. 703-706.

Goldbaum et al., Image Understanding for Automated Retinal Diagnosis, 1989, SCAMC, Proceedings, The 13th Annual Symposium on Computer Applications in Medical Care, pp. 756,760.

Li et al., Automatic Location of Optic Disk in Retinal Images, IEEE, Transactions on Image Processing, vol. 2, pp. 837-840, Oct. 7-10, 2001.

Hoover et al., Locating the Optic Nerve in a Retinal Image Using the Fuzzy Convergence of the Blood Vessels, IEEE, vol. 22, No. 8, pp. 951-958, Aug. 2003.

Foracchia et al., Detection of Optic Disc in Retinal Images by Means of a Geometrical Model of Vessel Structure, vol. 23, No. 10, pp. 1189-1195, Oct. 2004.

Abdel-Ghafar et al., Detection and Characterisation of the Optic Disk in Glaucoma and Diabetic Retinopathy, (2004).

Tobin et al., Characterization of the Optic Disc in Retinal Imagery using a Probabilistic Approach, Medical Imaging 2006: Image Processing, vol. 6144, pp. 1088-1097, Feb. 2006.

Karnowski et al., Locating the Optic Nerve in Retinal Images: Comparing Model-Based and Bayesian Decision Methods, IEEE Proceedings of the Int'l Conf of Engineering in Mediical and Biology Society, pp. 4436-4439, Aug. 2006.

Abramoff et al., The Automatic Detection of the Optic Disc Location in Retinal Images using Optic Disc Location Regression, Proceedings of the 28th IEEE EMBS Annual Int'l Conf, pp. 4432-4435, New York, NY, US, Aug. 30-Sep. 3, 2006.

Park et al., Locating the Optic Disc in Retinal Images, IEEE Proceedings of the Int' Conf on Computer Graphics, Imagine, and Visualisation, pp. 141-145, Jul. 26-28, 2006.

Tobin et al., Detection of Anatomic Structures in Human Retinal Imagery, IEEE Transactions on Medical Imaging, vol. 26, No. 12, pp. 1729-1739, Dec. 2007.

* cited by examiner

METHOD AND SYSTEM FOR ASSIGNING A CONFIDENCE METRIC FOR AUTOMATED DETERMINATION OF OPTIC DISC LOCATION

STATEMENT REGARDING FEDERALLY SPONSORED RESEARCH OR DEVELOPMENT

The United States Government has rights in this invention pursuant to contract no. DE-AC05-00OR22725 between the United States Department of Energy and UT-Battelle, LLC.

CROSS-REFERENCE TO RELATED APPLICATIONS

N/A

FIELD OF THE INVENTION

The invention relates to computer aided screening methods and devices for assigning a confidence metric for an automated determination of optic disc location.

BACKGROUND

The World Health Organization estimates that 135 million people have diabetes mellitus worldwide and that the number of people with diabetes will increase to 300 million by the year 2025. More than 18 million Americans currently have diabetes and the number of adults with the disease is projected to more than double by the year 2050. An additional 16 million adults between the ages of 40-74 have pre-diabetes and are at an elevated risk for developing diabetes. Visual disability and blindness have a profound socioeconomic impact upon the diabetic population and diabetic retinopathy (DR) is the leading cause of new blindness in working-age adults in the industrialized world. The prevalence rates for DR and vision-threatening DR in adults over age 40 is 40.3% and 8.2%, respectively. It is estimated that as much as $167 million dollars and 71,000-85,000 sight-years could be saved annually in the US alone with improved screening methods for diagnosing diabetic retinopathy.

Most current methods used to address screening for DR rely on either a patient visit to a physician specifically trained to diagnose eye disease from digital retinal photography, or the use of established retinal reading centers such as the Joslin Vision Network (Boston, Mass.), and Inoveon Corp. (Oklahoma City, Okla.). While reading centers have shown that digital photography is an effective tool for identifying DR when performed by experienced, certified readers, the turnaround time for a diagnosis is roughly 72 hours (3 days) on average.

Recently, research has been conducted to develop automated techniques to analyze retinal images for diagnosing some diseases having retinal manifestations. While these automated disease diagnosis techniques have shown promise, even the best still misdiagnose such diseases between 5 and 20% of the time. Whether the misdiagnosis is a false positive or a false negative, the risk of such an elevated error rate limits the commercial usefulness of current automated diagnosis techniques.

SUMMARY OF THE INVENTION

A method and system for assigning a confidence metric for automated, i.e., computer aided, determination of optic disc location. The method can include providing an image analysis system, having a processing apparatus programmed with a set of image analysis instructions stored in a computer-readable medium for carrying out the method. The method can include accessing a retinal image of a patient using said image analysis system. At least two sets of coordinates locating an optic disc in the retinal image can be determined using said image analysis system. A first set of coordinates can be determined using a first image analysis technique, and A second set of coordinates can be determined using a second image analysis technique that is different from the first image analysis technique. An accuracy parameter can be calculated using the sets of coordinates can be calculated and compared to a primary risk cut-off value. A high confidence level can be assigned to the retinal image if the accuracy parameter is less than the primary risk cut-off value. A low confidence level can be assigned to the retinal image if the accuracy parameter is greater than the primary risk cut-off value. The primary risk cut-off value can be selected to represent a value where the risk of a misdiagnosis using an automated disease diagnosis process meets a predetermined limit.

The entire method can be entirely automated. The accuracy parameter can be a parameter selected from the group including, but not limited to, average distance between sets of coordinates, standard deviation of the location represented by the sets of coordinates, and combinations thereof.

One of the first and second image analysis techniques can be a vascular-based technique. One of the first and second image analysis techniques can be a nonvascular-based technique. The first image analysis technique can be a vascular-based technique and the second image analysis technique can be a nonvascular-based technique.

The vascular-based technique can be selected from the group of techniques including a feature-based likelihood ratio (FBLR) methodology, a fuzzy convergence algorithm, a vessel segmentation technique, a combined vessel segmentation and regression technique, and combinations thereof. The nonvascular-based technique can be selected from the group of techniques including a principal component analyses (PCA) methodology, a PCA-linear discrimination analysis (LDA) technique, a PCA-LDR-likelihood ratio technique, a Hough transform technique, and combinations thereof.

The method can include determining a diameter of the optic disc and setting the primary risk cut-off value at three times the diameter of the optic disc. Where the accuracy parameter is distance, the primary risk cut-off value can be three times the average diameter of optic discs for a representative population.

If a high confidence level is assigned, the method can include analyzing the retinal image using an automated system for diagnosing a disease having retinal manifestations. If the analyzing step determines that a disease having retinal manifestations is present in the retinal image, the method can include flagging the retinal image for examination by an ophthalmic professional, transmitting the retinal image to a remote location for examination by an ophthalmic professional, or both. If a low confidence level is assigned, the method can include flagging the retinal image for examination by an ophthalmic professional for diagnosing a disease having retinal manifestations, transmitting the retinal image to a remote location for examination by an ophthalmic professional for diagnosing a disease having retinal manifestations, or both.

In some embodiments, the method can include determining a secondary risk cut-off value, wherein the secondary risk cut-off value can be selected to represent a value where the risk of a misdiagnosis using an automated disease diagnosis process meets a second predetermined limit, less than that of the primary risk cut-off value. The accuracy parameter can be compared to the primary risk cut-off value and the secondary risk cut-off value. A high confidence level can be assigned to the retinal image if the accuracy parameter is less than both the primary risk cut-off value and the secondary risk cut-off value. An intermediate confidence level can be assigned to the retinal image if the accuracy parameter is between the primary risk cut-off value and the secondary risk cut-off value. Finally, a low confidence level can be assigned to the retinal image if the accuracy parameter is greater than both the primary risk cut-off value and the secondary risk cut-off value.

In the three tiered embodiment, the retinal image can be flagged for examination by an ophthalmic professional for diagnosing a disease having retinal manifestations, if a low or intermediate confidence level is assigned. The retinal image can be transmitted to a remote location for examination by an ophthalmic professional, if a low or intermediate confidence level is assigned.

BRIEF DESCRIPTION OF THE DRAWINGS

A fuller understanding of the present invention and the features and benefits thereof will be accomplished upon review of the following detailed description together with the accompanying drawings, in which.

DETAILED DESCRIPTION OF THE INVENTION

A method for assigning a retinal image a confidence metric for automated determination of optic disc location is disclosed. The confidence metric indicates the relative likelihood that the optic disc has been located accurately and that a retinal image can be successfully diagnosed for a disease having retinal manifestations using an automated diagnostic method. The method can also be used for determining which retinal images require referral to an ophthalmic professional for diagnosis due to a high likelihood of a misdiagnosis of a disease having retinal manifestations using an automated disease diagnosis technique.

Figure 1:
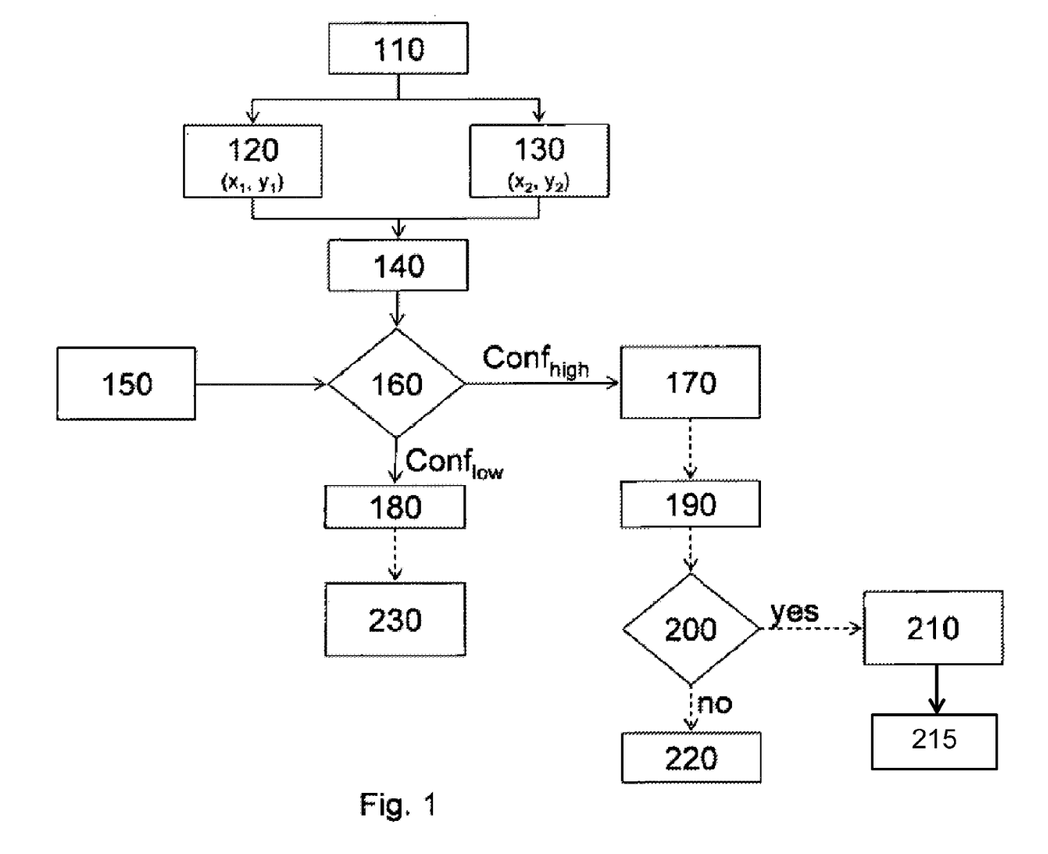
FIG. 1 is a flow chart depicting an exemplary embodiment of the instant invention.

As shown in FIG. 1, the method of assigning a confidence metric for automated determination of optic disc location using an automated disease diagnosis technique can include providing an image analysis system, comprising a processing apparatus programmed with a set of image analysis instructions stored in a computer-readable medium for carrying out the method. A retinal image of a patient can be accessed 110 using the image analysis system. At least two sets of coordinates, e.g., $(x_n, y_n)$, locating an optic disc in the retinal image can be determined 120 and 130, respectively, using the image analysis system. The first set of coordinates can be determined 120 using a first image analysis technique, and the second set of coordinates can be determined 130 using a second image analysis technique that is different from said first image analysis technique. An accuracy parameter can be calculated using the at least two sets of coordinates 140. A primary risk cut-off value can be selected 150 to represent a value where the risk of a misdiagnosis using an automated disease diagnosis process meets a predetermined limit. For example, the predetermined limit can be the point at which the risk of a misdiagnosis becomes unacceptably high, e.g., 20% chance of misdiagnosis or greater. The entire method can be entirely automated.

As used herein, "retinal images" include images capturing retinal structures, such as, but not limited to, fundus images. As used herein, a "set of coordinates locating an optic disc" is an xy-coordinate, e.g., $(x_n, y_n)$, used to locate the optic disc, e.g., the center of the optic disc. Although the sets of coordinates will generally be based on the center of the optic disc, other portions of the optic disc may be used so long as they can be accurately compared, such as an extreme portion of the optic disc, e.g. the top, bottom, extreme left or extreme right. In addition, it is possible that more than one set of coordinates could be used to calculate an accuracy parameter, such as the center, the top and the bottom of the optic disc. Each of these is encompassed by sets of coordinates locating an optic disc and any, or all, of these may be used to calculate an accuracy parameter.

The term "computer-readable medium" should be taken to include a single medium or multiple media (such as a centralized or distributed database, and/or associated caches and servers) that store the one or more sets of instructions. The term "computer-readable medium" shall also be taken to include any medium that is capable of storing, encoding or carrying a set of instructions for execution by the machine and that cause the machine to perform any one or more of the methodologies of the present disclosure.

The term "computer-readable medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape. Accordingly, the disclosure is considered to include any one or more of a computer-readable medium or a distribution medium, as listed herein and including art-recognized equivalents and successor media, in which the software implementations herein are stored.

The accuracy parameter can be a parameter selected from the group including, but not limited to, average distance between sets of coordinates (includes distance between two sets of coordinates), standard deviation of location of sets of coordinates, and combinations thereof. As used herein, "accuracy parameter" is intended to encompass any measures of accuracy of the location of the optic disc as determined by multiple, different image analysis techniques, including mathematical measures, e.g., distance between locations; statistical measures, e.g., standard deviation of locations, average distance between locations; and combinations thereof.

An accuracy parameter, such the average distance between the first and second set of coordinates, can be compared 160 to the primary risk cut-off value. If the distance is less than the primary risk cut-off value, a high confidence level can be assigned to the retinal image 170. If the distance is greater than the primary risk cut-off value, a low confidence level can be assigned to the retinal image 180.

The primary risk cut-off value can be selected 150 to represent a value where the risk of a misdiagnosis using an automated disease diagnosis process becomes unacceptably high. Where different image analysis techniques are used to independently determine the coordinate location of the optic disc, the distance between the two sets of coordinates, or another accuracy parameter, can be correlated with the probability that an automated disease diagnosis process that relies on retinal images will make a misdiagnosis. For example, using a study of the distance between two sets of coordinates using two different image analysis techniques, it is possible to determine an appropriate distance to select a primary risk cut-off value above which an unacceptably high percentage of misdiagnoses will occur using an automated disease diagnosis process. Although this is framed as selecting a primary risk cut-off value where the "risk of a misdiagnosis using an automated disease diagnosis process becomes unacceptably high" if the distance is greater than the primary risk cut-off value, it is equally true that the risk of a misdiagnosis using an automated disease diagnosis process can be sufficiently low if the distance is less than the primary risk cut-off value. It will be understood that any number of methods, including statistical methods, for evaluating the risk of misdiagnosis versus the calculated distance can be utilized to identify an appropriate primary risk cut-off value. It is to be understood that similar studies can be used to assign a primary risk cut-off value for other accuracy parameters. It should also be understood that similar techniques can be used for assigning values to other risk cut-off values, e.g., secondary risk cut-off values.

Figure 2:
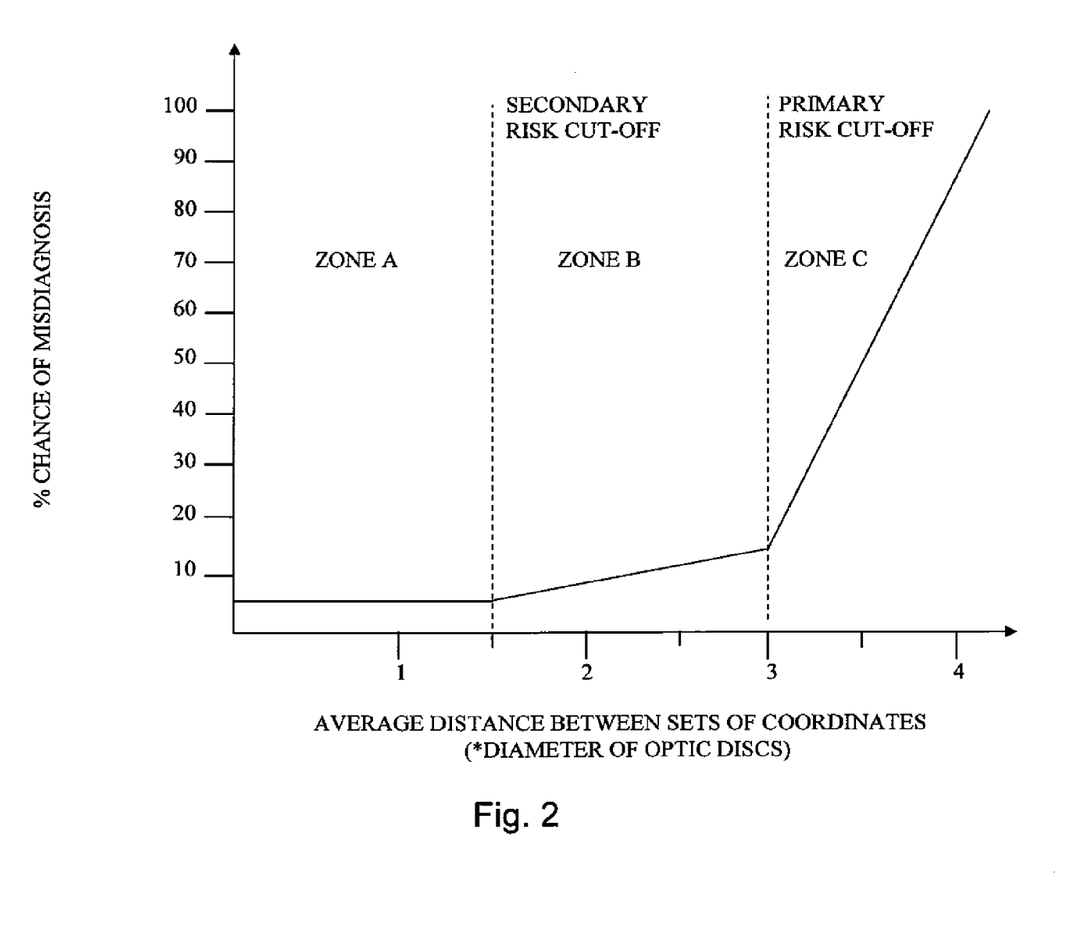
FIG. 2 is a chart showing a theoretical relationship of the chance of misdiagnosis of a disease having retinal manifestations and the distance between optic disc location determinations obtained using two different techniques.

The method can also include determining a secondary risk cut-off value, where the secondary risk cut-off value is selected to represent a value where the risk of misdiagnosis using an automated disease diagnosis process is significant but not unacceptably high. As with the primary risk cut-off value, the secondary risk cut-off value can be evaluated based on an acceptable level of risk and appropriate studies between accuracy parameter values and the likelihood of misdiagnosis using an automated disease diagnosis technique. FIG. 2 provides a hypothetical example using primary and secondary risk cut-off values where the accuracy parameter is average distance. In the example of FIG. 2, the risk of misdiagnosis can initially be relatively flat (zone A), followed by a gradual increase in risk as the distance increases (zone B), and finally a steep increase in risk as the distance gets even larger (zone C). In FIG. 2, the primary risk cut-off value is approximately 3 optic disc diameters and the secondary risk cut-off value is approximately 1.5 optic disc diameters, which in FIG. 2 correspond to a 15% chance misdiagnosis and a 5% chance of misdiagnosis, respectively.

The primary risk cut-off value and the secondary risk cut-off value can be an absolute value or a relative value. For example, the primary risk cut-off values can be some multiple of the optic disc diameter. The primary risk cut-off value and the secondary risk cut-off value can, independently, be any multiple of the optic disc diameter between one-quarter and four, in any increment, including halves, quarters, tenths, twentieths, hundredths, etc. For example, the primary and secondary risk cut-off values can be 0.56* [optic disc diameter], 2.72* [optic disc diameter], 3.98* [optic disc diameter], etc. In addition, the primary and secondary risk cut-off values can be 0.25 X, 0.5 X, 1 X, 1.25 X, 1.5X, 1.75X, 2 X, 2.25 X, 2.5 X, 2.75X, 3 X, 3.25 X, 3.5 X or 3.75 X, wherein X=[optic disc diameter]. The optic disc diameter used to determine the risk cut-off values can be an average optic disc diameter for a representative population of subjects. The optic disc diameter used to determine the risk cut-off values can be the diameter of the optic disc in the retinal image being evaluated. The primary and secondary risk cut-off values can be selected to correspond to any appropriate percent chance of misdiagnosis, e.g., less than 1%, less than 2%, less than 3%, less than 4%, less than 5%, less than 7%, less than 10.5%, less than 15%, etc.

The invention as described herein should be understood to encompass other embodiments where more than two risk cut-off values may are used. For example, it may be desirable to afford more than three levels of scrutiny depending on the objectives, anticipated patient volumes, and resources available to those implementing the method and system disclosed herein.

The method does not indicate which confidence level to assign where the accuracy parameter is equal to the primary or secondary risk cut-off value. It is to be understood that this decision can be made at the discretion of those employing the method based on the data used to assign the risk cut-off values and how the primary and secondary risk cut-off values are selected. Thus, it is possible for the confidence level falling on either side of a risk cut-off value to be assigned when the accuracy parameter is equal to the risk cut-off value.

Where a risk cut-off value is proportional to the diameter of the optic disc, the diameter of the optic disc can be calculated using one or more image analysis techniques. Where more than one image analysis technique is use to calculate the diameter of the optic disc, the diameters calculated using each image analysis technique can be combined or averaged in any appropriate manner.

The method can include determining the diameter of the optic disc in the retinal image and setting the primary risk cut-off value at three times the diameter of the optic disc and the secondary risk cut-off value at one and a half times the diameter. The method can include setting the primary risk cut-off value at three times the diameter of the optic disc of a representative population and the secondary risk cut-off value at one and a half times the diameter.

The method can also include analyzing 190 the retinal image using an automated system for diagnosing a disease having retinal manifestations, if a high confidence level is assigned. Any useful disease diagnosis method can be incorporated into the automated system for diagnosing a disease having retinal manifestations, including the method set forth in co-pending U.S. patent application Ser. No. 11/416,834, "Method and System for the Diagnosis of Disease Using Retinal Image Content and an Archive of Diagnosed Human Patient Data," filed by Tobin et al., the entirety of which is incorporated herein by references. If the retinal analysis using an automated diagnosis system determines that a disease having retinal manifestations is present in the retinal image 200, the retinal image can be flagged for examination by an ophthalmic professional 210. The method can also include transmitting 215 the retinal image to a remote location for examination by an ophthalmic professional, if the automated diagnosis system determines that a disease having retinal manifestations is present in the retinal image. If the automated diagnosis system determines that no disease having retinal manifestations is present in the retinal image, the retinal image can be classified accordingly 220.

Where a retinal image is assigned a low confidence level, the retinal image can be flagged 180 for examination by an ophthalmic professional for diagnosing a disease having retinal manifestations. Although not shown, retinal images assigned a low confidence level can be transmitted to a remote location for examination by an ophthalmic professional without flagging 180. Similarly, retinal images can be flagged 180 and subsequently transmitted 230 to a remote location for examination by an ophthalmic professional. As used herein, transmitted to a remote location is meant to include transmission using any computer network, whether wired or wireless, including the Internet, e-mail, downloading to flash memory or external hard drives, uploading to an file transfer protocol (ftp) or similar site, satellite transmission, and other transmission methods.

Figure 3:
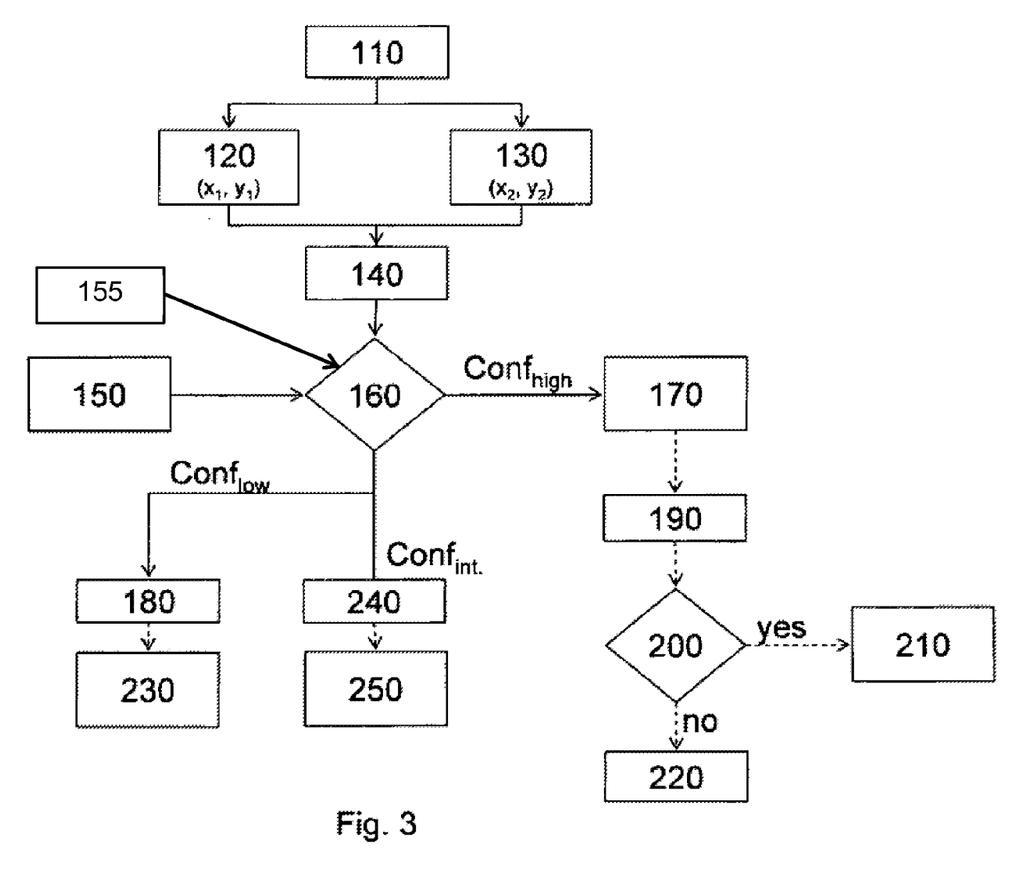
FIG. 3 is a flow chart depicting another exemplary embodiment of the instant invention.

As shown in FIG. 3, the method can include comparing 160 the accuracy parameter to the determined primary risk cut-off value 150 and the secondary risk cut-off value 155. If the accuracy parameter is less than both the primary risk cut-off value and the secondary risk cut-off value, a high confidence level can be assigned to the retinal image 170. If the accuracy parameter is between the primary risk cut-off value and the secondary risk cut-off value, an intermediate confidence level can be assigned to the retinal image 240. Finally, if the accuracy parameter is greater than both the primary risk cut-off value and the secondary risk cut-off value, a low confidence level can be assigned to the retinal image 180.

The method can include flagging the retinal image for examination by an ophthalmic professional for diagnosing a disease having retinal manifestations, if a low confidence level is assigned to the retinal image 180, an intermediate confidence level is assigned to the retinal image 240, or either confidence level 180 or 240 is assigned to the retinal image. Similarly, the retinal image can be transmitted to a remote location for examination by an ophthalmic professional for diagnosing a disease having retinal manifestations, if a low confidence level is assigned to the retinal image 230, an intermediate confidence level is assigned to the retinal image 250, or either confidence level 230 or 250 is assigned to the retinal image. Although not shown, the retinal images can be transmitted without being flagged. The flagged images may be viewed and analyzed locally by an ophthalmic professional.

The method can also include means for notifying the patient of the results of the automated process. For example, displaying or printing a result (positive or negative) of a disease diagnosis methodology, informing the patient that further consideration is required, or suggesting that the patient consult with an ophthalmic professional. Similarly, a patient can receive notification of the diagnosis via e-mail, text message, or other means of remote transmission.

At least one of the first and second image analysis techniques for locating the optic disc can be a vascular-based technique. At least one of the first and second image analysis techniques for locating the optic disc can be a nonvascular-based technique. In some embodiments, the first image analysis technique can be a vascular-based technique and the second image analysis technique can be a nonvascular-based technique. Using at least two distinct methods of locating the optic disc can provides a high likelihood that small distances between the coordinates of the optic disc obtained using the different techniques represent high confidence in the identified optic disc location. This is because different techniques are unlikely to make the same mistake in the process of identifying the optic disc. It has been determined that accurate detection of the optic disc location can be correlated to a lower likelihood of misdiagnosis using relevant automatic disease diagnosis systems for diagnosis diseases having retinal manifestations.

As used herein, "vascular-based techniques" include those techniques that rely primarily or entirely on the vasculature found in a retinal image. Exemplary vascular-based techniques include feature-based likelihood ratio (FBLR) methodologies, a fuzzy convergence algorithm, vessel segmentation techniques, combined vessel segmentation and regression analysis techniques, and combinations thereof. Some examples of these techniques can be found in U.S. patent application Ser. No. 11/416,834, "Method and System for the Diagnosis of Disease Using Retinal Image Content and an Archive of Diagnosed Human Patient Data," filed by Tobin et al.; Hoover et al., "Locating the Optic Nerve in a Retinal Image Using the Fuzzy Convergence of the Blood Vessels," IEEE Transactions on Medical Imaging, Vol. 22, No. 8 (August 2003); and Abramoff et al., "The Automatic Detection of the Optic Disc Location in Retinal Images Using Optic Disc Location Regression," $28^{th}$ IEEE EMBS Annual International Conference, Aug. 30-Sep. 3, 2006.

As used herein, "nonvascular-based techniques" include those techniques that rely primarily or exclusively on shapes of structures in the retinal image other than the vasculature. Exemplary nonvascular-based techniques include principal component analyses (PCA) methodologies, a PCA-linear discrimination analysis (LDA) approaches, PCA-LDR-likelihood ratio approaches, Hough transform approaches, and combinations thereof. Some examples of these techniques can be found in Li et al., "Automatic Location of Optic Disk in Retinal Images," 2001 International Conference on Image Processing, Vol. 2, Pages 837-840; Abdel-Gharaf et al., "Detection and Characterisation of the Optic Disk in Glaucoma and Diabetic Retinopathy," Proceedings Medical Image Understanding and Analysis, September, 2004; Park et al., "Locating the Optic Disc in Retinal Images," Computer Graphics, Imaging and Visualization, pages 141-145 (2006); and Karnowski et al., "Locating the Optic Nerve in Retinal Images: Comparing Model-Based and Bayesian Decision Methods," 28th Annual International Conf. of the IEEE EMBS (August 2006).

The invention also includes a system for assigning a confidence metric for accuracy of an automated determination of optic disc location. The system can include a computer system programmed with a routine set of instructions stored on a computer-readable medium. The computer system can include an image analysis system, having a processing apparatus programmed with a set of image analysis instructions stored in a computer-readable medium. In addition, the computer system can include structure for accessing a retinal image of a patient using the image analysis system and structure for determining at least two sets of coordinates locating an optic disc in the retinal image using the image analysis system, wherein a first set of coordinates is determined using a first image analysis technique, and a second set of coordinates is determined using a second image analysis technique different from said first image analysis technique. The computer system can include structure for calculating an accuracy parameter using the at least two sets of coordinates and comparing the accuracy parameter to a primary risk cut-off value; and structure for assigning a high confidence level to the retinal image if the accuracy parameter is less than the primary risk cut-off value, and assigning a low confidence level to the retinal image if the accuracy parameter is greater than the primary risk cut-off value. The computer system can also include structure for transmitting the retinal image to a remote location for examination by an ophthalmic professional, structure for determining a diameter of the optic disc, and structure and instructions stored on a computer-readable medium for carrying out any other steps described herein.

The method disclosed herein can be useful for high volume patient screening. For example, screening for diabetic retinopathy in non-traditional environments, such as grocery stores, department stores and malls. Regardless of location, the method can be employed using a kiosk that includes an integral fundus camera to obtaining retinal images of customers. The kiosk can then process the retinal images and determine whether there is a high likelihood of misdiagnosis. If the likelihood of misdiagnosis is low, an automatic disease diagnosis methodology can be used to diagnose this image. If the likelihood of misdiagnosis is high, the retinal image can be flagged for review by an ophthalmic professional at the kiosk or sent to a remote location for review by an ophthalmic professional. As will be apparent, any other features of the invention disclosed herein may be incorporated into this kiosk embodiment.

The method for assigning a confidence metric according to the invention is generally implemented on a computer system. The system can include memory (preferably non-volatile memory) which can store all necessary image analysis and disease diagnosis methodologies. The system can also include memory for storing the retinal images of one or more patients. The system can also include an integrated camera for taking retinal images, such as a fundus camera, and structure for communicating to the images obtained using the integrated camera to the computer system for the image analysis methodologies described herein. Similarly, the system can include a remote camera and structure for transmitting the images to a remote location where the computer system is located.

The computer system can include a processor (such as a central processing unit (CPU)), a graphics processing unit (GPU, or both), a main memory and a static memory, which communicate with each other via a bus. The computer system may further include a video display unit (such as a liquid crystal display (LCD)), a flat panel, a solid state display, or a cathode ray tube (CRT)). The computer system can include an input device (such as a keyboard), a cursor control device (such as a mouse), a disk drive unit, a signal generation device (such as a speaker or remote control) and a network interface device.

The disk drive unit may include a computer-readable medium on which is stored one or more sets of instructions (such as software) embodying any one or more of the methodologies or functions described herein, including those methods illustrated above. The instructions can also reside, completely or at least partially, within the main memory, the static memory, and/or within the processor during execution thereof by the computer system. The main memory and the processor also can constitute computer-readable media.

Dedicated hardware implementations including, but not limited to, application specific integrated circuits, programmable logic arrays and other hardware devices can likewise be constructed to implement the methods described herein. Applications that can include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein can be operated as software programs running on a computer processor of the computer system. Furthermore, software implementations can include, but are not limited to, distributed processing or component/object distributed processing, parallel processing, or virtual machine processing can also be constructed to implement the methods described herein.

The present disclosure contemplates a computer-readable medium containing instructions, or that which receives and executes instructions from a propagated signal so that a device connected to a network environment can send or receive voice, video or data, and to communicate over the network using the instructions. The instructions can further be transmitted or received over a network via the network interface device.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

We claim:

1. A method for assigning to a retinal image a confidence metric for automated determination of optic disc location, comprising:
    accessing a retinal image of a patient using an image analysis system;
    determining at least two sets of coordinates locating an optic disc in the retinal image using said image analysis system, wherein a first set of coordinates is determined using a first image analysis technique, and a second set of coordinates is determined using a second image analysis technique that is different from said first image analysis technique;
    calculating an accuracy parameter of the at least two sets of coordinates;
    comparing the accuracy parameter to a primary risk cut-off value; and
    assigning a high confidence level to the retinal image if the accuracy parameter is less than the primary risk cut-off value, and assigning a low confidence level to the retinal image if the accuracy parameter is greater than the primary risk cut-off value, wherein the primary risk cut-off value is selected to represent a value where the risk of a misdiagnosis using an automated disease diagnosis process meets a predetermined limit.

2. The method of claim 1, wherein one of the first and second image analysis techniques is a vascular-based technique.

3. The method of claim 2, wherein the vascular-based technique comprises a methodology selected from the group consisting of a feature-based likelihood ratio (FBLR) methodology, a fuzzy convergence algorithm, a vessel segmentation technique, a combined vessel segmentation and regression technique, and combinations thereof.

4. The method of claim 1, wherein one of the first and second image analysis techniques is a nonvascular-based technique.

5. The method of claim 4, wherein the nonvascular-based technique comprises a methodology selected from the group consisting of a principal component analyses (PCA) methodology, a PCA-linear discrimination analysis (LDA) technique, a PCA-LDR-likelihood ratio technique, a Hough transform technique, and combinations thereof.

6. The method of claim 1, wherein the first image analysis technique is a vascular-based technique and the second image analysis technique is a nonvascular-based technique.

7. The method of claim 1, further comprising: determining a diameter of the optic disc, wherein the accuracy parameter is the average distance between the at least two sets of coordinates and the primary risk cut-off value is three times the diameter of the optic disc.

8. The method of claim 1, wherein the accuracy parameter is the average distance between the at least two sets of coordinates and the primary risk cut-off value is three times the average diameter of optic discs for a representative population.

9. The method of claim 1, further comprising: analyzing the retinal image using an automated system for diagnosing a disease having retinal manifestations, if a high confidence level is assigned.

10. The method of claim 9, further comprising: flagging the retinal image for examination by an ophthalmic professional, transmitting the retinal image to a remote location for examination by an ophthalmic professional, or both, if the analyzing step determines that a disease having retinal manifestations is present in the retinal image.

11. The method of claim 1, further comprising: flagging the retinal image for examination by an ophthalmic professional for diagnosing a disease having retinal manifestations, transmitting the retinal image to a remote location for examination by an ophthalmic professional for diagnosing a disease having retinal manifestations, or both, if a low confidence level is assigned.

12. The method of claim 1, wherein the entire method is entirely automated.

13. The method of claim 1, wherein the accuracy parameter comprises a parameter selected from the group consisting of average distance between sets of coordinates, standard deviation of location of sets of coordinates, and combinations thereof.

14. The method of claim 1, wherein the comparing step further includes comparing the accuracy parameter to a secondary risk cut-off value; and the method further comprises: assigning an intermediate confidence level to the retinal image, if the accuracy parameter is between the primary risk cut-off value and the secondary risk cut-off value, wherein the secondary risk cut-off value is selected to represent a value where the risk of a misdiagnosis using an automated disease diagnosis process meets a second predetermined limit greater than the risk corresponding to the primary risk cut-off value.

15. The method of claim 14, further comprising: flagging the retinal image for examination by an ophthalmic professional for diagnosing a disease having retinal manifestations, if a low confidence level is assigned, if an intermediate confidence level is assigned, or if either a low or intermediate confidence level is assigned.

16. The method of claim 14, further comprising: transmitting the retinal image to a remote location for examination by an ophthalmic professional, if a low confidence level is assigned, if an intermediate confidence level is assigned, or if either a low or intermediate confidence level is assigned.

17. A system for assigning to a retinal image a confidence metric for automated determination of optic disc location, comprising:
- a computer system programmed with a routine set of instructions stored in a computer-readable medium, said computer system comprising:
  - an image analysis system, comprising a processing apparatus programmed with a set of image analysis instructions stored in a computer-readable medium for assigning said confidence metric;
- structure for accessing a retinal image of a patient using said image analysis system; structure for determining at least two sets of coordinates locating an optic disc in the retinal image using the image analysis system, wherein a first set of coordinates is determined using a first image analysis technique, and a second set of coordinates is determined using a second image analysis technique different from said first image analysis technique;
- structure for calculating an accuracy parameter of the at least two sets of coordinates and comparing the accuracy parameter to a primary risk cut-off value; and
- structure for assigning a high confidence level to the retinal image if the accuracy parameter is less than the primary risk cut-off value, and assigning a low confidence level to the retinal image if the accuracy parameter is greater than the primary risk cut-off value, wherein the primary risk cut-off value is selected to represent a value where the risk of a misdiagnosis using an automated disease diagnosis process meets a predetermined limit.

18. The system of claim 17, wherein the computer system further comprises: structure for transmitting the retinal image to a remote location for examination by an ophthalmic professional.

19. The system of claim 17, wherein the computer system further comprises: structure for determining a diameter of the optic disc.

20. The system of claim 17, wherein:
- the structure for comparing further comprises structure for comparing the accuracy parameter to a secondary risk cut-off value; and
- the structure for assigning further comprises structure for assigning an intermediate confidence level to the retinal image, if the accuracy parameter is between the primary risk cut-off value and the secondary risk cut-off value, wherein the secondary risk cut-off value is selected to represent a value where the risk of a misdiagnosis using an automated disease diagnosis process meets a second predetermined limit greater than the risk corresponding to the primary risk-cut-off value.

* * * * *